US00PP35532P3

(12) United States Plant Patent
Olesen

(10) Patent No.: US PP35,532 P3
(45) Date of Patent: Dec. 12, 2023

(54) ROSE PLANT NAMED 'POULREN040'

(50) Latin Name: *Rosa hybrida*
Varietal Denomination: Poulren040

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/803,620

(22) Filed: Sep. 13, 2022

(65) Prior Publication Data

US 2023/0103287 P1 Mar. 30, 2023

(30) Foreign Application Priority Data

Sep. 24, 2021 (QZ) ..... PBR 2021/2353

(51) Int. Cl.
*A01H 5/02* (2018.01)
*A01H 6/74* (2018.01)

(52) U.S. Cl.
USPC ..... Plt./136
CPC ..... *A01H 6/749* (2018.05)

(58) Field of Classification Search
USPC ..... Plt./101, 130, 136
See application file for complete search history.

*Primary Examiner* — Karen M Redden

(57) ABSTRACT

A new garden rose plant of the hybrid tea class which has abundant, salmon pink flowers and attractive foliage. This new and distract variety has shown to be uniform and stable in the resulting generations from asexual propagation.

2 Drawing Sheets

Botanical designation: *Rosa hybrida.*

Variety denomination: 'Poulren040'.

This application claims priority to Plant Breeder's Rights Application Number 2021/2353, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of (crossing year) and the resulting seeds were planted in a controlled environment in Fredensborg, Denmark. The new variety, named 'Poulren040', originated as a single seedling from the stated cross.

The new variety may be distinguished from its male pollen parent and female seed parent primarily by the following characteristics. The male pollen parent plant has pink flowers while the new variety has salmon pink flowers. While the female seed parent plant is a miniature rose, the claimed plant is a hybrid tea shrub.

The objective of the hybridization of this rose variety was to create a new and distinct variety with unique qualities, such as:

1. Uniform and abundant salmon pink flowers;
2. Vigorous, but compact growth when propagated on its own roots;
3. Exceptional disease resistance; and
4. Strong flower perfume.

This combination of qualities is not present in previously available commercial cultivars of this type, known to the inventor, and distinguish 'Poulren040' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulren040' was selected in the spring of 2014 by the inventor as a single plant from the progeny of the aforementioned hybridization.

Asexual reproduction of 'Poulren040' by rooted cuttings was first done by Mogens N. Olesen in the nursery in Fredensborg, Denmark in July, 2014. This initial and other subsequent asexual propagations conducted in controlled environments have demonstrated that the characteristics of 'Poulren040' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren040'.

Specifically illustrated in FIG. 1 of the drawings are mature and juvenile leaves and bare stems, and a cluster of open flowers on a branch.

Figure 1:
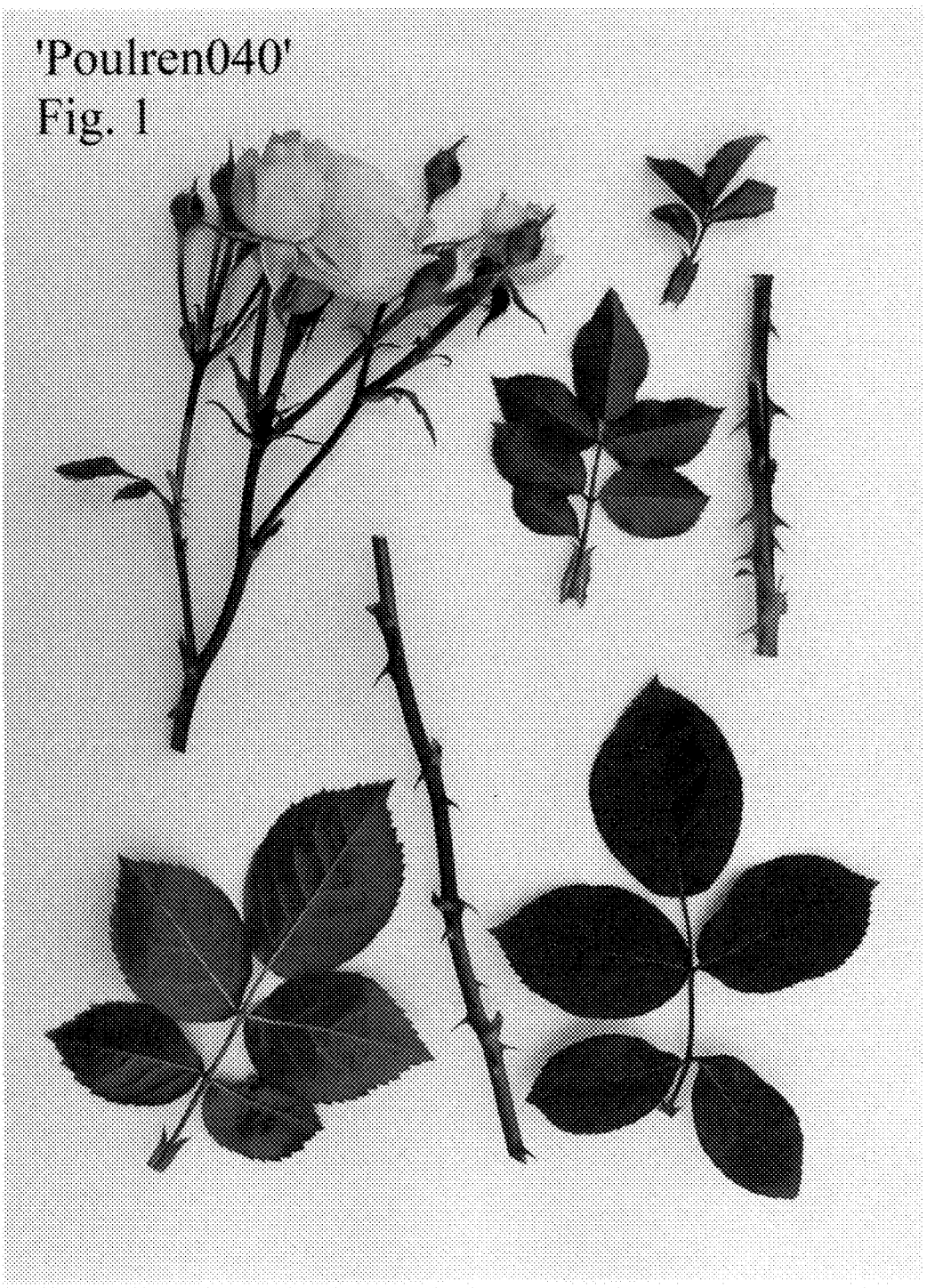
Figure 2:
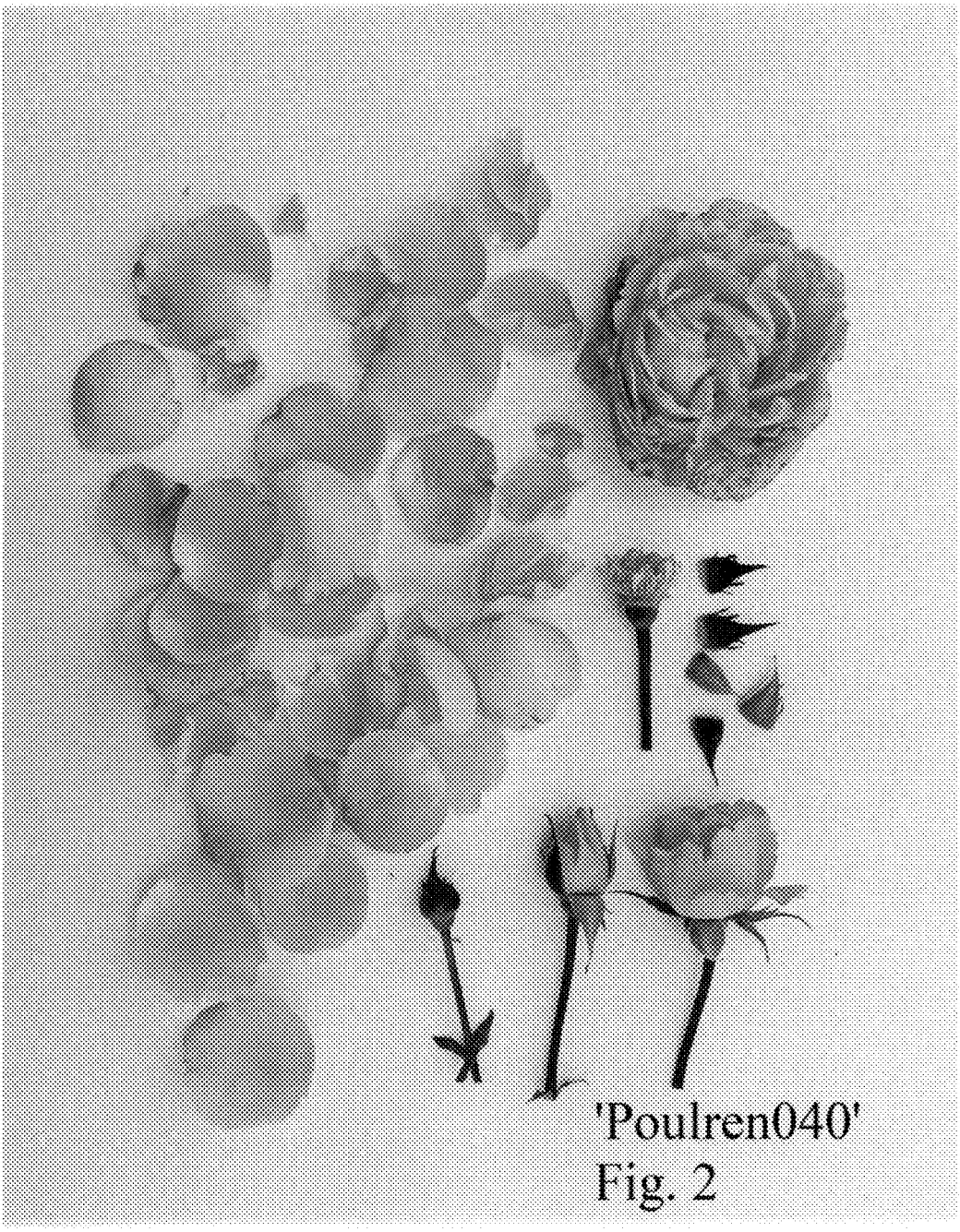

Specifically illustrated in FIG. 2 of the drawings are an open flower viewed from above, sepals detached revealing reproductive flower parts, flower bud and partially open flowers, and flower petals detached. Plants shown are 2 years of age.

DETAILED DESCRIPTION OF THE VARIETY

The following is a description of 'Poulren040', as observed in its growth in a field nursery in Linn County, Oregon. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulen011', U.S. Plant Pat. No. 15,167 are now compared to 'Poulren040'. In terms of general flower tonality, the claimed plant is Red Group 49A. The comparison variety has a general flower tonality of Red Group 54D. While the claimed plant has flowers with 50 petals, the comparison variety has 80 petals.

FLOWER AND FLOWER BUD

Blooming habit: Continuous.

Flower bud:

- *Size.*—Upon opening, 19 mm in length from base of receptacle to end of bud. Bud diameter is 12 mm.
- *Bud form.*—Ovoid.
- *Bud color.*—As sepals divide petals are Red Group 38A and Red Group 53B.
- *Sepal inner surface.*—Color: Yellow-Green Group 146D with intonations of Greyed-Purple Group 183A. Surface: Lightly pubescent.
- *Sepal outer surface.*—Color: Yellow-Green Group 144A with intonations of Greyed-Red Group 183A. Texture: Smooth.
- *Sepal shape.*—Apex: Cirrhose. Base: Flat at union with receptacle.
- *Sepal margin.*—Margins have moderate foliaceous appendages on three of the five sepals.
- *Sepal size.*—About 26 mm long, 14 mm wide.
- *Receptacle.*—Texture: Smooth. Size: 7 mm in height, 10 mm wide. Color: Yellow-Green Group 144A with intonations of Greyed-Purple Group 183C. Shape: Campanulate.
- *Pedicel.*—Surface: Smooth. Length: 50 mm. Diameter: 3 mm on average. Color: Yellow-Green Group 144A with intonations of Greyed-Purple Group 183B. Strength: Strong.
- *Peduncle.*—Length: 30 to 50 mm. Diameter: About 4 mm. Color: Yellow-Green Group 144A with strong intonations of Greyed-Purple Group 183B. Texture: Smooth.

Flower bud development: Flower buds are borne in clusters of 7 on average. Development as a thyrse.

Flower bloom:

- *Fragrance.*—Very strong rose perfume.
- *Duration.*—The blooms have a duration on the plant of approximately 15 days. Petals fall cleanly away from plant after flowers have fully matured.
- *Size.*—Flower diameter is 80 mm when open. Flower depth is 35 mm.
- *Flower shape.*—Quartered, deep cup, very double, with many overlapping petals packed into quarter sections.
- *Shape of flower, side view.*—The upper and lower portions are flat.

Petalage: Under normal conditions, flowers have about 50 petals.

General tonality of flower: Open flowers are Red Group 49A. After flowers have fully matured tonality remains the same.

Petal color:

- *Upon opening, outer petals.*—Upper surface: Red Group 43D. Lower surface: Red Group 53A. Guard petals have intonations of Red Group 53D in streaks.
- *Upon opening, inner petals.*—Upper surface: Red Group 48C. Lower surface: Red Group 48C.
- *Basal petal spots, upon opening.*—Upper surface: Yellow Group 4D. Lower surface: Yellow Group 1D.
- *After opening, outer petals.*—Upper surface: Red Group 52D. Lower surface: Red Group 56A.
- *After opening, inner petals.*—Upper surface: Red Group 52D. Lower surface: Red Group 56A.
- *Basal petal spots, after opening.*—Upper surface: Green-White Group 157D. Lower surface: Green-White Group 157D.

Petals:

- *Petal reflex.*—Somewhat reflexed.
- *Margin.*—Numerous clefts and strong undulations.
- *Shape.*—Broad and elliptic. Apex shape: Rounded. Base shape: Acute.
- *Size.*—About 44 mm (l)×50 mm (w).
- *Texture.*—Smooth.
- *Thickness.*—Average.

Petaloids:

- *Size.*—25 mm (l) by 20 mm (w).
- *Quantity.*—About 7.
- *Shape.*—The apex is divided by a deep cleft.
- *Color.*—Red Group 48C on upper and 1. Yellow Group 1D at the point of attachment.

Reproductive flower parts:

- *Pollen.*—None observed.
- *Anthers.*—Size: 2.5 mm in length. Color: Yellow Group 12B. Quantity: 45 on average.
- *Filaments.*—Color: Red Group 50D. Length: 6 mm.
- *Pistils.*—Length: 9 mm. Quantity: 34 on average.
- *Stigmas.*—Color: Orange-White Group 159C.
- *Styles.*—Color: Green-White Group 157A with intonations of Red-Purple Group 58C.
- *Location of stigmas.*—Level in location relative to the length of the filaments and the height of the anthers.
- *Hips.*—None Observed.

PLANT

Plant growth: Upright. Plants are 55 cm in height, and 59 cm wide.

Stems:

- *Color of juvenile growth.*—Yellow-Green Group 144A with strong intonations of Greyed-Purple Group 183A.
- *Color of mature growth.*—Yellow-Green Group 146B with strong intonations of Greyed-Purple Group 183A.
- *Length.*—Canes are about 25 cm from the base of the plant to the flowering portion.
- *Diameter.*—About 6 mm.
- *Internodes.*—On mature canes about 38 to 43 mm between nodes.
- *Surface texture.*—Young wood: Smooth. Older wood: Smooth.

Long prickles:

- *Incidence.*—11 prickles per 10 cm of stem.
- *Size.*—Average length of prickles on mature stems is 8 mm.
- *Shape.*—Upper portion is linear. Lower portion is concave.

*Color*.—Juvenile prickles: Greyed-Purple Group 183B. Mature prickles: Greyed-Purple Group 183B.

Plant foliage:

*Compound leaf*.—About 145 mm (l)×125 mm (w).

*Quantity*.—2 leaves per 10 cm of stem on average.

*Leaf bearing angle to the stem*.—45 degrees.

*Color of juvenile foliage*.—Upper side: Yellow-Green Group 146A shaded with Greyed-Purple Group 183A. Lower side: Yellow-Green Group 146C shaded with Greyed-Purple Group 183A.

*Color of mature foliage*.—Upper side: Yellow-Green Group 147A. Lower side: Yellow-Green Group 147B.

Plant leaves and leaflets:

*Stipules*.—Size: About 10 mm long, mm wide. Quantity: 2 per compound leaf. Shape: Linear, slightly broad based with outward extending apices. Margins: Finely serrated. Color: Yellow-Green Group 144A.

*Petiole*.—Length: About 31 mm. Diameter: 2 mm. Upper surface color: Yellow-Green Group 144A. Lower surface color: Yellow-Green Group 144A.

*Rachis*.—Length: About 40 mm. Upper surface color: Yellow-Green Group 144A. Lower surface color: Yellow-Green Group 144A. Lower surface texture: Prickles 4 mm, Greyed-Red 181D.

*Leaflet*.—Quantity: Normally 5 leaflets. Margins: Serrated. Size: Terminal leaflets are about 74 mm long, 50 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren040' substantially as described and illustrated herein.

* * * * *

'Poulren040'

'Poulren040'